(12) United States Patent
Briggs et al.

(10) Patent No.: US 11,198,901 B2
(45) Date of Patent: Dec. 14, 2021

(54) METHOD FOR FORMING NANO-GAPS IN GRAPHENE

(71) Applicant: OXFORD UNIVERSITY INNOVATION LIMITED, Oxford (GB)

(72) Inventors: George Andrew Davidson Briggs, Oxford (GB); Jan Andries Mol, Oxford (GB)

(73) Assignee: OXFORD UNIVERSITY INNOVATION LIMITED, Oxford (GB)

( * ) Notice: Subject to any disclaimer, the term of this patent is extended or adjusted under 35 U.S.C. 154(b) by 0 days.

(21) Appl. No.: 15/321,836

(22) PCT Filed: Jun. 23, 2015

(86) PCT No.: PCT/GB2015/051818
§ 371 (c)(1),
(2) Date: Dec. 23, 2016

(87) PCT Pub. No.: WO2016/005726
PCT Pub. Date: Jan. 14, 2016

(65) Prior Publication Data
US 2017/0145483 A1    May 25, 2017

(30) Foreign Application Priority Data

Jul. 11, 2014  (GB) ...................................... 1412356
Apr. 7, 2015   (GB) ...................................... 1505908

(51) Int. Cl.
| | | |
|---|---|---|
| B82Y 40/00 | (2011.01) | |
| H01L 29/45 | (2006.01) | |
| C12Q 1/6825 | (2018.01) | |
| G01N 33/487 | (2006.01) | |
| G01N 27/414 | (2006.01) | |
| B82Y 15/00 | (2011.01) | |
| H01L 51/05 | (2006.01) | |

(Continued)

(52) U.S. Cl.
CPC ............ *C12Q 1/6825* (2013.01); *B82Y 15/00* (2013.01); *B82Y 40/00* (2013.01);
(Continued)

(58) Field of Classification Search
CPC ............ C12Q 1/6825; C12Q 2565/631; G01N 27/3278; G01N 27/44791;
(Continued)

(56) References Cited

U.S. PATENT DOCUMENTS

| | | | |
|---|---|---|---|
| 2010/0144535 A1* | 6/2010 | Strachan | ............. B81C 1/00126 505/100 |
| 2012/0145549 A1* | 6/2012 | Cho | ................. G01N 33/48721 204/603 |

(Continued)

FOREIGN PATENT DOCUMENTS

| | | | |
|---|---|---|---|
| CN | 101156228 A | 4/2008 | |
| CN | 102456702 A | 5/2012 | |

(Continued)

OTHER PUBLICATIONS

J. Moser, et al., Current-induced cleaning of graphene, Applied Physics Letters, vol. 91, p. 163513-1-3 (2007) (Year: 2007).*

(Continued)

*Primary Examiner* — Maris R Kessel
(74) *Attorney, Agent, or Firm* — Eversheds Sutherland (US) LLP

(57) ABSTRACT

The present invention relates to a method for forming nano-gaps in graphene. The method may include applying a voltage across a region of graphene such that a nano-gap which extends across the entire width of the graphene is formed, wherein the region across which the voltage is applied may include a point which is the narrowest in the region.

14 Claims, 10 Drawing Sheets

(51) Int. Cl.
*H01L 51/00* (2006.01)
*G01N 27/447* (2006.01)
*H01L 21/321* (2006.01)
*H01L 51/10* (2006.01)
*C01B 32/194* (2017.01)
*H01L 29/16* (2006.01)
*H01L 29/76* (2006.01)

(52) U.S. Cl.
CPC ... *G01N 27/4146* (2013.01); *G01N 27/44791* (2013.01); *G01N 33/48721* (2013.01); *H01L 21/321* (2013.01); *H01L 29/456* (2013.01); *H01L 51/0045* (2013.01); *H01L 51/0595* (2013.01); *C01B 32/194* (2017.08); *H01L 29/1606* (2013.01); *H01L 29/7613* (2013.01); *H01L 51/0092* (2013.01); *H01L 51/0094* (2013.01); *H01L 51/0545* (2013.01); *H01L 51/105* (2013.01)

(58) Field of Classification Search
CPC ........ G01N 27/48721; G01N 33/48721; H01L 21/321; H01L 29/456; H01L 29/7613; B82Y 5/00; B82Y 15/00; B82Y 30/00; B82Y 4/00
See application file for complete search history.

(56) References Cited

U.S. PATENT DOCUMENTS

2013/0270521 A1  10/2013  Peng et al.
2013/0309776 A1* 11/2013  Drndic ................... G01N 27/26
                                                         436/94

2014/0125310 A1  5/2014  Lee et al.

FOREIGN PATENT DOCUMENTS

CN    102630304 A    8/2012
WO    2011046706 A1  4/2001
WO    2011046706 A1  4/2011

OTHER PUBLICATIONS

J. Baldwin, et al. Effects of Strain on Notched ZigZag Graphene Nanoribbons, Crystals, vol. 3, pp. 38-48 (2013).*
D. Johnston et al., Parallel Fabrication of Nanogap Electrode, Nano. Lett., vol. 7, No. 9, pp. 2774-2777 (2007) (Year: 2007).*
J. Moser, et al., Fabrication of large addition energy quantum dots in graphene, Appl. Phys. Lett., vol. 95, 173506 (2009) (Year: 2009).*
Cornelia Nef et al: "High-Yield Fabrication of nm-Size Gaps in Monolayer CVD graphene", Nanoscale, vol. 6, No. 13, May 22, 2014.
Ferry Prins et al: "Room Temperature Gating of Molecular Junctions Using Few-Layer Graphine Nanogap Electrodes", Nano Letters, vol. 11, No. 11, Nov. 9, 2011.
Enrique Burzuri et al: "Characterization of Nanometer-Spaced Few-Layer Graphene Electrodes", Graphene, vol. 01, No. 02, Oct. 10, 2012.
Shouvik Banerjee et al: "Electrochemistry at the Edge of a Single Graphene Layyer in a Nanopour", ACS Nano, vol. 7, No. 1, Dec. 18, 2012.
CN First Office Action and Search Report, CN 201580037412.5, dated Sep. 5, 2018 (15 pp.).

* cited by examiner

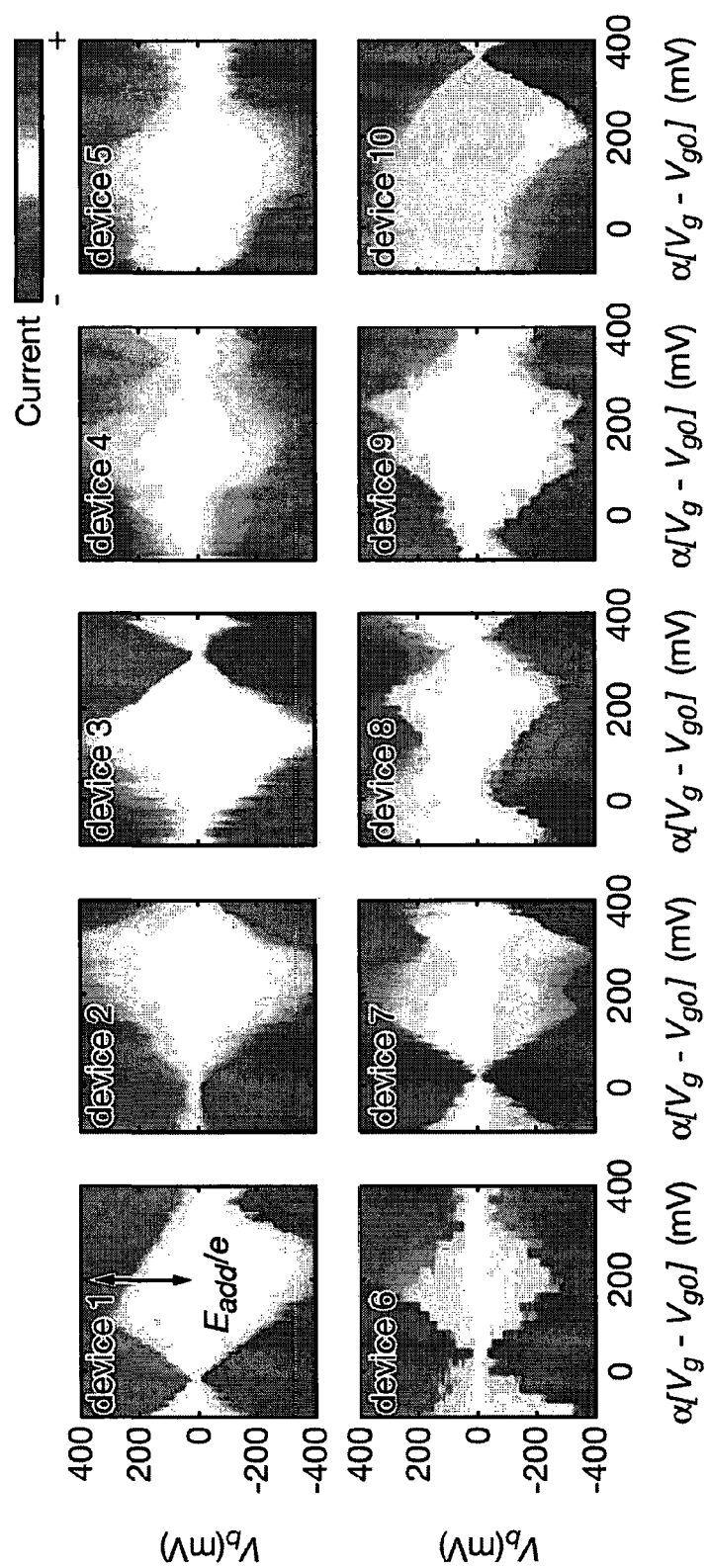

METHOD FOR FORMING NANO-GAPS IN GRAPHENE

TECHNICAL FIELD

The present invention relates to methods for forming nano-gaps in graphene, more especially the production of graphene electrodes and devices comprising them.

BACKGROUND OF THE INVENTION

Integrated circuits where each functional unit is formed by only a single molecule are considered the ultimate form of electronic device scaling. Experimental demonstrations of molecular device functionality include rectifiers, switches and transistors, and effects of quantum interference have been observed in charge transport through single molecules. To harness the full potential of individual molecules, there exists a need for robust and identical devices (e.g. three-terminal devices), including the provision of alternative electrode materials that are stable at room temperature. Graphene is a promising candidate for the replacement of metal electrodes because of the high-temperature stability of the covalent bond-structure, the ability to anchor diverse molecules via functionalization, either covalently or using $\pi$-$\pi$ stacking, and the reduced screening of the gate-field due to the extreme thinness of the electrodes (as little as a single atomic layer). Wafer-scale growth and integration of graphene with conventional silicon electronics have recently been demonstrated.

Two distinct approaches towards the fabrication of graphene-based molecular junctions are emerging. The first of these is based on plasma-etching of chemical vapour deposition (CVD) grown graphene point contacts. By over-etching, the lithographically defined pattern produces nano-gaps that are less than or equal to a nanometer and the position of the gaps can be controlled, albeit at the cost of yield with devices formed via this method having a yield of around 33%. An alternative approach is based on a process known as electroburning, which relies on the current-induced breakdown of graphene. While this method can give a high yield and allows some control over the size of the nano-gaps (e.g. by varying partial pressure of oxygen), the position of the nano-gaps fabricated is not well controlled due to the random nature of the electroburning process. This is a problem as many applications of graphene nano-gaps, e.g. use as electrodes, require precise positioning of the gap which can be reproduced on a large scale.

There thus exists a need for a process for forming graphene nano-gaps that provides a viable route for achieving controllable, high-yield, reproducible fabrication on a wafer scale.

The inventors have surprisingly found that a nano-gap fabrication strategy comprising subjecting specially shaped graphene sheets to an electroburning process (e.g. feedback-controlled electroburning) can produce accurately controlled nano-gaps in graphene sheets. The process achieves precise control over the size and position of the nano-gaps at higher yields than previously reported.

SUMMARY OF THE INVENTION

Thus, viewed from a first aspect, the present invention provides a method for forming nano-gaps in graphene, said method comprising applying a voltage across a region of graphene (or passing a current through said region) such that a nano-gap which extends across the entire width of the graphene is formed, wherein the region across which the voltage is applied (or through which the current is passed) comprises a point which is the narrowest in said region. While the method as herein described is conveniently described as involving the application of a voltage across the specified region of the graphene, it can equally be viewed as involving the passing of a current through the region. This will be clear to those skilled in the field due to the well-known relationship between voltage and current and the present disclosure should be interpreted accordingly.

Because the resulting graphene structure comprises graphene with a nano-gap in it, the method of the invention can also be viewed as a method for the formation of a graphene structure, e.g. a graphene sheet comprising a gap extending across the width of the sheet, a pair of graphene sheets separated by a nano-gap, or graphene electrodes separated by a nano-gap. Successive gaps can be formed in the same sheet or in separate (e.g. adjacent) sheets, and the geometries and relative orientations of the gaps can be chosen as required for specific applications.

The method of the invention is characterised in that the graphene to which the voltage is applied contains a point which is narrower than all others in the region across which the voltage is applied (the width being the dimension perpendicular to the direction of the voltage). The inventors have found that the gap forms at this narrowest point, therefore, by using graphene of a suitable shape, the position of the nano-gap can be controlled. Any shape which comprises such a narrow point can be used, however, it is most conveniently achieved by using a "notched" shape, i.e. a shape (e.g. rectangle, square or any other regular or irregular or amorphous shape) from which a notch has been removed along one of the edges (i.e. removal of a triangle with the apex pointing away from the edge of the sheet). Notched ribbons are especially preferred, i.e. the graphene is preferably in the shape of a rectangle from which a notch has been removed from one of the long edges. FIG. 5($a$) gives an example of a notched ribbon shape.

The graphene or graphene sheet may comprise more than one atomic layer of graphene, e.g. it may be "few-layer graphene" (FLG), especially graphene comprising 1 to 50, especially 1 to 20, preferably 1 to 5 layers, e.g. 1 or 2 layers. Especially preferably, it is single layer graphene (SLG). The sheet may comprise elements other than carbon, either due to carbon atoms being replaced with other atoms, functionalization of graphene, or due to sheets of materials other than graphene being present. Preferably the sheet consists essentially of graphene; preferably the sheet does not contain impurities, i.e. it is substantially free from impurities.

The method of the invention involves application of a voltage to the graphene such that a gap is formed, i.e. current-induced gap formation, which is known in the field as "electroburning". Without wishing to be bound by theory, it is thought that formation of the nano-gap is mediated by the breaking of carbon-carbon bonds at the edge of the graphene (edge-carbon atoms are more reactive due to incomplete $sp^2$-hybridization). Surprisingly, rather than the expected gradual narrowing of the sheet due to breakdown of the edge bonds, the nano-gap formation process of the present invention proceeds via a crack developing across the narrowest region of the graphene (see, for example, FIG. 3($d$)). In this way, the position of the narrowest point (which can be predetermined, e.g. by lithography) can determine the precise position of the nano-gap, thus achieving control of nano-gap position previously unobtainable. Thus, the present invention can be viewed as the use of a narrow point, e.g. a notch, to control the position of gap formation in graphene.

Electroburning is a method similar in some respects to electromigration, i.e. a process where the current in the system is increased until electrical breakdown. In the method of the invention a voltage is applied across a region of the graphene. The voltage causes a current to flow through the graphene, which results in a current which causes electrical breakdown, i.e. current-induced formation of a gap in the graphene. Controlling the voltage is preferred as it does not require active stabilization. By measuring the current (or alternatively, the resistance) during the voltage increase, the point at which breakdown occurs can be monitored as a (sudden or gradual) decrease in current will be observed. The method of the present invention involves this process being carried out across a region of the graphene which contains a point of minimum width and as described above, it is at this point that the gap is formed.

Due to the inversely proportional relationship between current and resistance, references herein to measurement of current should be understood to apply to measurement of resistance and vice versa. Similarly, references to increase in current should be understood to correspond to decreases in resistance and vice versa.

The electroburning process may be carried out in any suitable atmosphere. Although the term "electroburning" suggests that the process should be carried out in a chemically reactive atmosphere, for example one including oxygen (e.g. air), the term should be understood to cover the process carried out in other atmospheres such as molecular or atomic hydrogen or in a low or high vacuum (in which case the term "electroburning" is a convenient label by analogy).

In a preferred aspect, the electroburning step is feedback controlled. Thus, preferably, the process of voltage application comprises:
  (a) increasing the voltage while recording the current (or resistance);
  (b) decreasing the voltage when said current drops (or said resistance increases) and
  repeating steps (a) and (b) until a gap has formed.

The features of the electroburning process and feedback control will be primarily discussed herein with regard to alteration of voltage and measurement of current. However, due to the relationship between voltage, current and resistance, the invention should be understood to be equally applicable to the method where current is altered and voltage is measured (for example, if this is more convenient due to the equipment used).

Thus, the above preferred aspect of the process can be viewed as involving:
  (a) increasing the current while recording the voltage;
  (b) decreasing the current when said voltage rises; and
  repeating steps (a) and (b) until a gap has formed.

Feedback control allows for more precise control over the gap size. The determination of the point at which the voltage should be reduced is based on the point at which the current is observed to drop, e.g. when the change in current meets a pre-determined feedback condition. The feedback condition is thus set to control at what point the voltage should be reduced, e.g. decreased quickly ("ramped down") to zero.

Preferably the voltage (or current) ramp (i.e. step (a) above) is applied multiple times, with the feedback condition applied at each application. Thus, preferably, steps (a) and (b) are carried out from 1 to 500, preferably 2 to 100, especially 5 to 50 times. However, the use of the feedback control means that the number of cycles does not need to be predetermined. A further feedback criterion may be used to determine when a gap of the required size has formed.

Preferably, the resistance is measured during the voltage application. Gap formation can be determined by measurement of the resistance. A gap will be formed when the low-bias resistance exceeds a certain level, e.g. 100-1000 MΩ, preferably 300-500 MΩ. The low-bias I-V (current vs voltage) characteristic can be further analyzed between each cycle of the electroburning process (i.e. after each (a)-(b) sequence, for example by using the theory of quantum tunneling across a gap, e.g. use of the Simmons model), to give a more accurate determination of the size of the gap which has been created.

The nano-gap formed by the method of the invention is a gap which extends across the full width of the graphene. The length of the gap will therefore correspond to the width of the graphene at the narrowest point prior to electroburning. The width of the gap, i.e. the spacing between the two pieces of graphene which result from electroburning is typically 0.1 to 5 nm, preferably 0.5 to 2.5 nm, particularly 1 to 2 nm.

The graphene may be produced by any method, e.g. flakes, or CVD-grown graphene. CVD-grown graphene is preferred as it can be produced on a large scale. The graphene is preferably grown on copper, e.g. liquid copper or copper foil however other CVD substrates, such as nickel, silicon, silicon carbide or germanium are also suitable. The graphene is typically grown from methane. A mixture of methane:argon in a 1:4 ratio is a particularly suitable starting material. Typical flow rates for operation of the CVD furnace are 80 sccm of hydrogen and 10 sccm of methane, preferably at atmospheric pressure. Typical temperatures for operation of the CVD furnace are 500 to 2000° C., preferably 800 to 1200° C., e.g. around 1090° C.

The graphene is preferably deposited on a substrate prior to gap formation. Any method known in the art may be used, however use of support polymers such as poly(methyl methacrylate) (PMMA), thermal release tape or PDMS (polydimethylsiloxane) to facilitate the transfer of graphene onto a substrate is especially preferred. This involves coating (e.g. by spinning) the graphene with the support polymer and removing the previous substrate (i.e. copper or nickel). Preferred means of removing the previous substrate include etching, e.g. etching of copper with chemicals such as ammonium persulfate (e.g. 0.1M solution). The coated graphene is then strong enough to be transferred to another substrate without damaging the material. Before transfer to another substrate, the graphene and support are preferably rinsed, e.g. with deionised water in order to remove any traces of the CVD substrate.

Where the graphene sheet is deposited on a substrate prior to gap formation, the substrate is preferably selected from silicon substrates, e.g. doped silicon, or pre-pattered $Si/SiO_2$ chips, sapphire, quartz, silicon carbide, silicon nitride, germanium or diamond, optionally coated, e.g. with thermal oxide. Preferably the substrate is a silicon substrate. The substrate, e.g. silicon chip, preferably comprises electrical contacts, e.g. electrodes. Such contacts may be patterned onto the substrate using lithography (e.g. electron beam lithography or photo lithography) and/or metal (e.g. gold, chromium and/or titanium) evaporation. Especially preferred contacts are pairs of Cr/Au electrodes.

The graphene used in the process of the present invention is specially shaped such that there is a narrow point either side of which voltage can be applied. By "either side" is mean that the places at which the voltage is applied are wider than the narrow point, i.e. the voltage is not applied along the narrowest dimension, but across it, i.e. spanning it. In order for the position of gap-formation to be controllable, the narrow point should be a minimum (of graphene width)

in the region across which voltage is applied, i.e. it should produce a "bottle neck" of current density. By using a sharp corner in the shape of the constriction, an enhanced effect of current concentration can be achieved, as shown in FIGS. 3(c) and (d) (although this figure is shown for a symmetrical double notch, the principle applies equally to the asymmetrical notch geometries illustrated in FIG. 5).

As graphene is essentially two dimensional, the terms "graphene" and "graphene sheet" can be used interchangeably. Similarly, the shapes are described two-dimensionally, e.g. a graphene "ribbon" is a sheet which is longer than it is wide. In this context, the "width" is the dimension perpendicular to the direction of the voltage. Typical sheet dimensions are 0.5 to 50 µm, especially 1 to 10 µm (length) by 0.1 to 20 pm, especially 0.5 to 5 µm (width). Typical widths at the narrowest point are 50 to 500 nm, especially around 200 nm.

Although regular shapes (not taking into account the narrow point), e.g. rectangles, squares, etc. are preferred for the graphene, other regular or irregular shapes, e.g. circular, oval and amorphous may also be used, provided they comprise a narrow point either side of which voltage can be applied. Ribbons, e.g. rectangles, are especially preferred. The narrow point in the graphene (e.g. sheet or ribbon) may be formed by a cut-out, e.g. a notch as exemplified by FIG. 5(a), a "bow-tie", i.e. two notches opposite one another as in FIG. 1(c), a curved cut-out (see FIG. 5(b)) but any shape with a narrowed point or constriction is suitable. A ribbon comprising a notch (e.g. as in FIG. 5(a)) is especially preferred. Such a "notched" ribbon shape can be described as a ribbon/rectangle from which a notch has been removed along one of the long edges (i.e. removal of a triangle with the apex pointing away from the edge of the sheet).

Sheets with more than one narrow point may be used, e.g. where more than one gap is desired, however, in order for the position of gap formation to be controlled, the region across which voltage is applied should contain a single narrowest point (i.e. application of voltage across a region with multiple narrow points of equal width leads to uncertainty regarding at which the gap will form). Applying the voltage across each narrow point separately enables multiple gaps to be formed in an array with control over their position. An example of a suitable shape is shown in FIG. 5(c) which shows a sheet shape that could be used to produce a three-terminal device.

The graphene may be shaped lithographically, for example, by exposing a negative resist using electron beam lithography followed by oxygen plasma etching. This may be followed by an optional annealing step (e.g. at 350° C. for 1 h in an inert, e.g. argon, atmosphere) to remove residual resist.

The application of a voltage to the graphene in order to induce gap-formation may be carried out in any suitable atmosphere, for example air, e.g. at atmospheric pressure, or in atomic or molecular hydrogen, or in a vacuum. The applicant has surprisingly found that the method can be carried out in air (i.e. no special atmosphere or vacuum is necessary) and this is therefore preferred for convenience.

The voltage increase may be at any convenient rate, depending on the apparatus used. Typical rates of voltage increase ("ramping-up") are 0.2 to 5 V/s, preferably 0.5 to 1.0 V/s, e.g. around 0.75 V/s. In instances where it is the current that is altered, corresponding current increase rates are typically used, e.g. 0.01 mA/s to 0.5 mA/s, preferably 0.05 mA/s to 0.1 mA/s, especially preferably 0.075 mA/s.

Measurement of the current during the voltage application (or vice versa if applicable) may be carried out continuously or substantially continuously, e.g. using a sampling rate of 50 to 300 µs, e.g. 100 to 200 µs, especially around 200 µs. An I-V curve may be measured between applications of the voltage to form the gap, i.e. after each (or some) of the cycles of steps (a)-(b).

When feedback control is used, a feedback condition is set, i.e. the point at which the voltage needs to be returned to zero. The feedback condition can be set at a drop $\Delta I_{set}$ of the current within a amount of voltage increase, e.g. a drop of 6 to 15 µA, especially 9 to 12 µA within the past 15 mV. The feedback condition can be constant throughout the process of gap-formation. Optionally, to adjust the rate at which the gap is formed (e.g. to prevent the graphene from electroburning too abruptly at the initial voltage ramps or to avoid decreasing the voltage due to a current increase that is merely due to signal noise) the feedback condition can be adjusted for each voltage ramp depending on the threshold voltage ($V_{th}$) at which the previous current drop occurred. This typically involves the feedback condition being set at a smaller current drop value for the initial cycles of steps (a) and (b) (i.e. when the current is high) and being increased in later cycles as current decreases and thus the possibility of a "drop" being due to signal noise is greater. Typical such feedback conditions are $\Delta I_{set}$=6, 9, 12 and 15 µA for $V_{th}$ 1.9, 1.6, 1.3 and 1.0 V respectively.

When the feedback condition is met, i.e. the current starts to fall, indicating that electrical breakdown is about to occur, the voltage is ramped down, i.e. decreased, preferably to zero. The rate at which this is carried out depends on the apparatus used, but typical decrease rates are 100 to 500 V/s, especially 200 to 300 V/s, e.g. around 225 V/s. In instances where it is the current that is altered, corresponding current decrease rates are typically used, e.g. 10 mA/s to 50 mA/s, especially 20 mA/s to 30 mA/s, preferably around 22.5 mA/s.

In an especially preferred method of the invention, feedback-controlled electroburning is applied across a notched region of graphene by applying a voltage across the notched area and ramping up the voltage at a rate of around 0.75 v/s, while at the same time monitoring the current. When a pre-set feedback condition, e.g. of a 6 µA drop within the past 15 mV, is met, the voltage is then quickly ramped down to zero. After each voltage ramp, the device's resistance is measured and the process (of ramping the voltage up until the current drops and then back down to zero) is repeated until the low-bias resistance exceeds a pre-set level which is indicative of nano-gap formation.

Characterization of the nano-gaps may be carried out using a similar set-up to that used for the feedback controlled electroburning. Measurement of current-voltage curves in this way has been found to produce non-Ohmic I-V traces which are characteristic of transport through a single tunnel junction (see FIG. 2). The size of the tunnel-barrier can be estimated by fitting the I-V traces to the Simmons model using the barrier height, width and asymmetry as fitting parameters (see FIG. 6).

Thus, in a preferred implementation, an I-V curve may be measured between applications of the voltage to form the gap, i.e. between each or some of the cycles of steps(a) and (b). The I-V data are analysed using the quantum theory of tunnelling through a gap to determine the size of the gap, as illustrated in FIG. 2. Because of the exponential dependence of tunnelling current density on gap size, this determination will be dominated by the narrowest part of the gap. Such analysis can be used to give a more precise criterion for the size of gap created, and hence for the feedback control to terminate the growth of the gap. At this point, the size of the gap can be determined, e.g. using the Simmons model, and a decision can be taken whether to continue the electroburning process further (e.g. if a larger gap size than that calculated is desired).

A preferred aspect of the method of the invention therefore involves the width of the nano-gap being determined by analyzing an I-V measurement (after a voltage ramp or between voltage ramps).

Thus, viewed from a further aspect, the present invention provides a method for controlling the size of nano-gaps in graphene, said method comprising steps as herein described while measuring a current-voltage trace and using said trace to calculate predicted gap-size.

In another preferred implementation, the approach of the gap formation can be anticipated from a characteristic jump in the conductance, as illustrated in FIG. 6. It has been observed that in the last stages of gap formation there can be a decrease in current followed by an increase, as illustrated in FIG. 6(d). This phenomenon can be used in advanced control to indicated when the formation of the gap is imminent and affords the method of the invention excellent reproducibility. Thus the I-V traces recorded prior to gap formation (such as those in FIGS. 1(f) and 6(d)) can be used to determine when gap formation is approaching.

A preferred aspect of the method of the invention therefore involves changes in the conductance being used to determine the onset of gap formation.

Due to its reproducibility, the method of the invention can be used for the large scale fabrication of graphene nano-gaps. Arrays of gaps can be produced on a single substrate, e.g. a wafer or chip, e.g. using an automated probe-station. The fact that the method of the invention allows for the control of gap position and gap size, means that arrays of selected design can be produced. The present invention therefore provides a method for preparing nano-gap arrays on graphene comprising the steps as herein described, including controlling the position and size of the gaps.

The graphene may be functionalized (i.e. prior to or subsequent to gap formation), e.g. chemically functionalized, to form, for example, graphene oxide. The functionalization may comprise the introduction of functional groups at the edges of the graphene. Typical functional groups in this regard are carboxyl groups, acid chloride groups, amide groups and the like. Functionalization may also involve grafting to polymers, full hydrogenation to form graphane, partial hydrogenation to form hydrogenated graphene or the analogous halogenations e.g. to form graphene halides (e.g. fluoro graphene) or halogenated, e.g. fluorinated graphene. The graphene of the invention can also act as a ligand to coordinate metals (e.g. copper or nickel ions) and metal ions by introducing functional groups.

The invention therefore enables the fabrication of single layer graphene nano-gaps by applying the method of feedback-controlled electroburning to notched ribbon devices, which are plasma etched from CVD grown graphene that is wet-transferred onto pre-patterned metal electrodes. As already mentioned, the method allows for control over the size and position of the nano-gaps which has, until now, not been achievable. This enables the reproducible formation of nano-gaps in graphene, thus allowing arrays of nano-gaps to be formed according to any design.

A graphene structure comprising a nano-gap (e.g. a gap of 0.1 to 5 nm, especially preferably 0.5 to 2.5 nm, particularly 1 to 2 nm) wherein said structure is obtained or obtainable by any of the methods herein described thus forms a further aspect of the present invention.

Viewed from a further aspect, the present invention provides a graphene structure comprising a nano-gap, e.g. a gap of 0.1 to 5 nm, especially preferably 0.5 to 2.5 nm, particularly 1 to 2 nm.

Graphene sheets comprising a gap can also be viewed as a pair of graphene sheets, or pair of graphene electrodes. The graphene structures of the invention therefore include graphene comprising a nano-gap, a graphene sheet comprising a nano-gap extending across the width of the sheet, a pair of graphene sheets separated by a nano-gap, graphene electrodes separated by a nano-gap and graphene nano-gap arrays. Typical dimensions and shapes for the graphene structures, e.g. sheets, of the invention are as described above.

A further aspect of the invention provides an array of devices comprising graphene electrodes as herein described. Particularly preferred are such arrays in which the gap sizes differ by less than 50%, especially less than 30%, preferably less than 10%, especially preferably less than 5%.

As noted herein, the invention provides a method for controlling the size and/or position of nano-gaps in graphene. The control over gap size and position makes the graphene structures of the invention useful for a variety of electronic applications, e.g. those involving contacting molecules in devices with aligned gates. Devices, e.g. electronic and/or molecular devices or electronic circuits, comprising the graphene structures of the invention therefore form a further aspect of the present disclosure.

Viewed from a further aspect, the present invention provides the use of the graphene structures (e.g. graphene nano-gaps, graphene sheets, graphene electrodes) as herein described in devices, especially electronic and/or molecular devices or in electronic circuits. Similarly, the invention provides a method for the production of such devices, said method comprising forming a nano-gap according to the present invention. Devices comprising the graphene structures (e.g. graphene nano-gaps, graphene sheets, graphene electrodes) as herein described form a further aspect of the invention. Examples of preferred devices are chips, rectifiers, switches, transistors and sensors, e.g. devices for analysing macromolecules, especially biomolecules such as DNA or RNA. The gap sizes formed make the graphene nano-gaps particularly suitable for contacting single molecules in molecular devices. Single molecule electronic devices, such as single-molecule single-electron transistors, rectifiers and switches, are therefore particularly preferred devices of the invention. Especially preferred are devices comprising "graphene-molecule-graphene" units.

As previously mentioned, molecules can be anchored to the graphene structures of the invention either by covalent C—C bonding or preferably by ττ-ττ stacking, which is thought to leave the electronic structure of the molecule largely unchanged. Suitable molecules for use in single molecule devices are known in the art and typically comprise a molecular backbone with specific side-groups for anchoring, spacing and self-alignment with the graphene. So-called "molecular wires" and macromolecules are examples of suitable structures. Especially suitable are molecules comprising a central backbone moiety attached to anchor groups, preferably via a spacer, e.g. hydrocarbyl spacer such as —$CH_2$—C≡C—. The anchor groups assist in attaching the molecules to the graphene electrodes, thus allowing the molecule to bridge the nano-gap. This results in single electron transport. The molecules may also comprise other side groups such as hydrophobic chains. Particularly suitable molecules for the devices of the present invention include those based on (e.g. in which the central backbone moiety is selected from) porphyrins, fullerenes, phthalocyanines, anthraquinones and derivatives thereof. Porphyrin molecules have been found to be especially preferred, e.g. the molecule shown in in FIG. 7, which contains a zinc-porphyrin backbone with tetrabenzofluorene "butterfly" anchor groups and hydrophobic side groups. It has been surprisingly found that the molecules herein described enable the charge transport through devices, such as the single-electron transistor of Example 5, to be largely insensitive to the atomic configuration of the graphene electrodes, resulting in reproducible single electron charging. The molecules may be placed in the nano-gaps by contacting the nano-gaps with a solution of the molecule. As molecules of the sort herein described are shown to be self-aligning in the nano-gaps (see Example 5), this provides a convenient means of assembling single molecule devices.

The devices of the present invention may comprise, in addition to the graphene structures of the invention, typical components for electronic devices, for example the substrates and electrical contacts described. An example of a device according to the present invention is shown in FIG. 7b which depicts a single-molecule single-electron transistor (SET) comprising graphene nano-gaps formed according to the present invention. The SET includes a heavily doped silicon chip with a 300 nm silicon oxide layer used as a back gate to modulate charge transport through the device.

Combining single molecules with the novel two-dimensional materials of the present invention and semiconductor fabrication technologies provides an attractive platform with which to realize scalable room-temperature single-electron transistor networks. Such an architecture may consist of individual molecules coupled to each other via graphene leads, with nearby graphene gate-electrodes (comprising the nano-gaps as herein described) to tune the orbital energy levels of the individual molecules. The gate-electrodes can be separated from the molecules by a two-dimensional insulator, to enable strong capacitive coupling between the gate and the molecule and allow the single-molecule transistors to exhibit gain. The reproducible method for graphene nano-gap formation of the present invention therefore allows for the production of reproducible devices, such as the single-molecule transistor discussed in Example 5. The present invention therefore providing a basis for the development of single-molecule electronics, single-molecule based sensors and spin-based quantum computations.

Use of the graphene structures (e.g. nano-gaps, graphene sheets, graphene electrodes) as herein described in methods and devices for sequencing DNA or RNA is especially preferred. Suitable circuits are integrated circuits, silicon logic circuits, integrated molecular circuits, e.g. those for use in analysing macromolecules, especially biomolecules such as DNA or RNA.

It is particularly advantageous that the current-voltage characteristics prior to gap formation and afterwards can be compared. In addition to using these measurements to determine the dimensions of the gap, changes in the characteristics can be measured and used in methods for detecting the present of anything in the gap. For example, a tunnelling current is generated when a molecule is in the gap, hence passing molecules through gaps and measuring the current enables characterization and has utility e.g. in DNA sequencing. FIG. 4 shows an example of a device for such a method. A notched ribbon of graphene is subjected to the method of the present invention in order to form a nano-gap, thus transforming the notched ribbon into a pair of graphene electrodes. Application of a voltage across the electrodes enables changes in the current to be detected and such changes can be attributable to the present of molecules or other substances in the gap. In FIG. 4, a strand of DNA is shown in the gap. As the strand passes through the gap, the tunnelling current will change depending on which part of the molecule (e.g. base) is involved. Recording the changes in current can therefore provide information as to the sequence of the bases in the DNA strand.

Thus, use of the graphene structures of the invention in a method for analysing macromolecules, especially biomolecules such as DNA or RNA (preferably sequencing of DNA or RNA) forms a further aspect of the invention. Viewed from a yet further aspect, the invention provides a method of detecting or characterizing a molecule in a sample, said method comprising contacting said sample with a graphene structure comprising a nano-gap as herein defined and detecting or measuring a change in voltage or a current (e.g. a tunnelling current) across the gap, wherein detection of a change in voltage or current (e.g. a tunnelling current) indicates the presence of a molecule in the sample, or enables the characteristics of the molecule to be determined. Typically, the molecule is characterized by changes in voltage or current as the molecule passes through the nano-gap.

Preferred molecules are macromolecules, e.g. biomolecules, especially DNA or RNA, in which case the characteristics of the molecule which are determined can be the sequence of bases. In a particularly preferred aspect the invention provides a method for determining the bases of DNA or RNA based on measuring the change in the voltage or current (e.g. tunnelling current) across a graphene structure of the invention.

For the types of analysis method herein described, graphene devices comprising more than one nano-gap in an array may be of particular interest and form a further aspect of the invention. Such devices may be formed from sheets placed over one another, e.g. as in FIG. 5(d).

As shown in the following examples, the present invention provides a method for the large scale fabrication of CVD graphene nano-gaps with a high yield, through a combined approach of lithographically-defined plasma-etching and feedback-controlled electroburning. Atomic force microscopy (AFM) images display a nano-gap located at the narrowest part of the graphene notched ribbon. The excellent control over the gap size and position makes this technique an attractive candidate for contacting molecules in devices with well aligned gates. Use of CVD graphene means that this technique can be scaled up using wafer-scale grown graphene. The passive-first-active-last process adopted in this technique enables integration into conventional silicon logic circuits. This scalable approach enables the use of graphene electrodes for large-scale integrated molecular circuits.

BRIEF DESCRIPTION OF THE DRAWINGS

The invention will now be further described in the following non-limiting Examples and with reference to the Figures.

a) Chemical structure of the molecular wire with a zinc-porphyrin backbone (black), 'butterfly' anchor groups (green, i.e. tetrabenzofluorene) and lipophilic side groups (red, i.e. containing Si). The functional groups allow for a robust, self-aligning mechanism.

b) Schematic of the single-molecule transistor. A heavily doped silicon chip with a 300 nm silicon oxide layer is used as a back gate to modulate charge transport through the device.

c) DFT simulations of LDOS for HOMO and LUMO iso-surfaces.

d) Typical room temperature current-voltage (I-V) traces before (green and blue, i.e. the middle and lower trace on the right of the plot) and after (red, i.e. the upper trace on the right of the plot) depositing molecules. The observed increase in current and noise after exposing the nano-gaps to the porphyrin solution is representative for all devices measured. The device was measured twice after exposing it to pure chloroform (green and blue, as above) to ensure that the nano-gaps did not change before exposing it to the porphyrin solution.

FIG. 8: Stability diagram of ten single-molecule transistors of Example 5. The source-drain current I as a function of source-drain bias $V_b$ and gate voltage $V_g$. All devices shown are in the weak-coupling regime where the current I≈pA-nA, meaning that an electron tunnels from the source electrode to the molecule, and then on to the drain, in a sequential process. Sequential electron tunnelling leads to diamond shaped regions where charge transport is Coulomb blocked.

Figure 4:
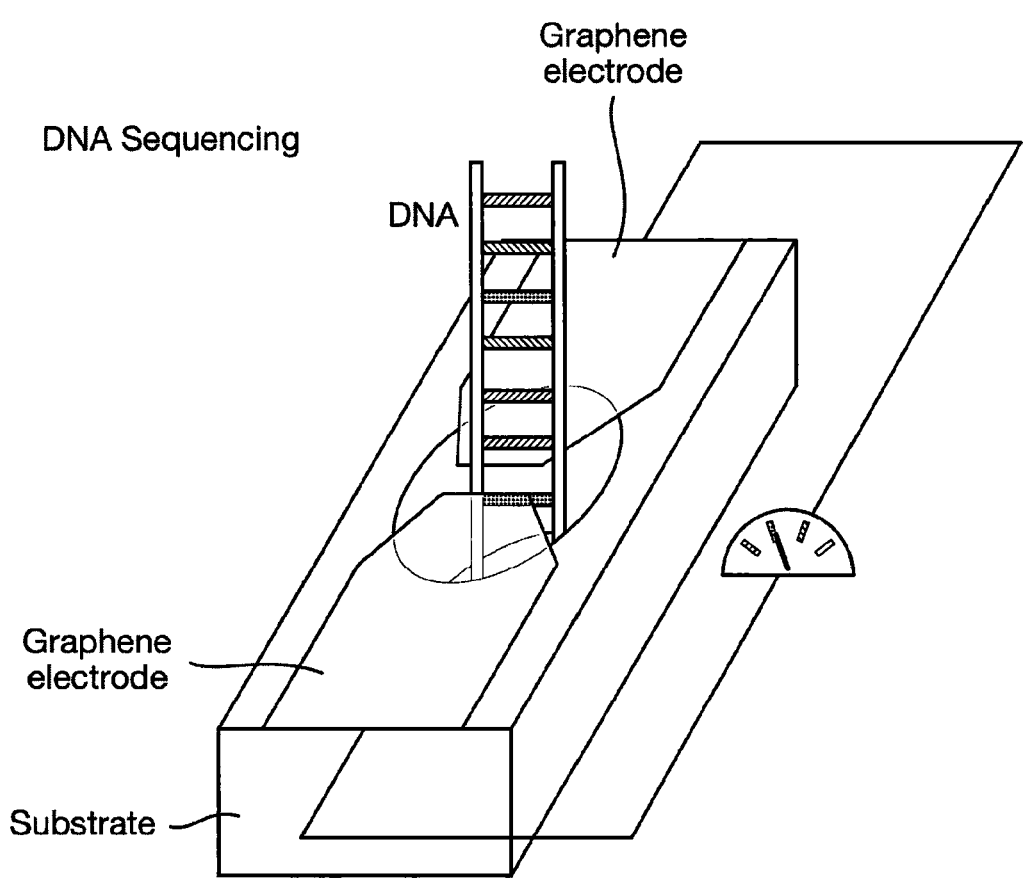
FIG. 4: Use of graphene electrode in method for DNA sequencing.
Figure 5A:
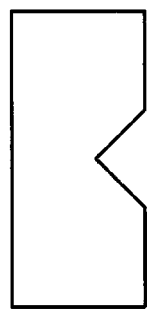
FIG. 5: Examples of geometries for graphene sheet(s) prior to gap formation.
Figure 5B:
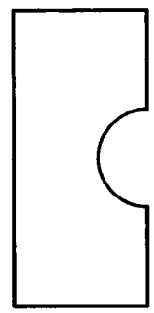
Figure 5C:
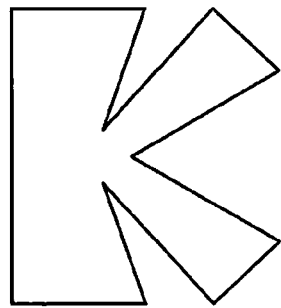
Figure 5D:
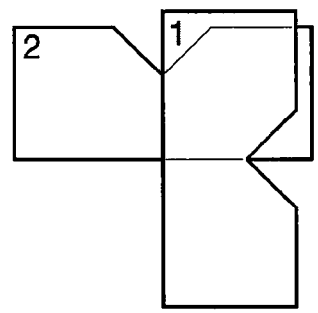
Figure 6A:
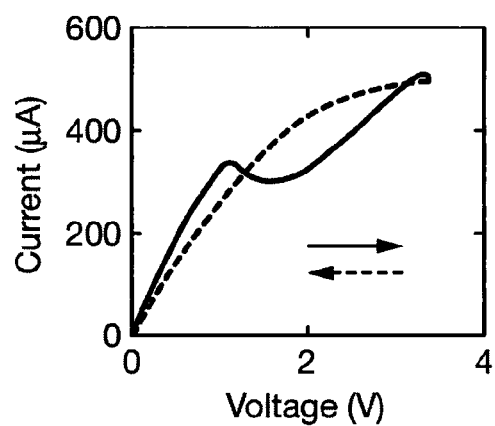
FIG. 6: Current-voltage (I-V) traces of feedback-controlled electroburning. (a) The first voltage ramp shows a distinct bump attributed to current annealing of the graphene sheet. (b-c) After the initial current annealing the conductance decreases after each voltage ramp. (c) The I-V traces eventually become non-Ohmic. (d) Just before breaking there is a sharp jump in the current.
Figure 6B:
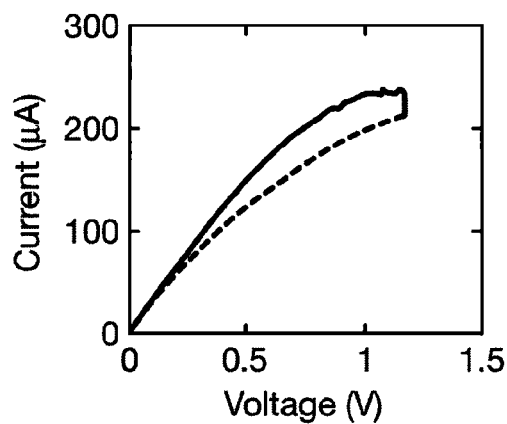
Figure 6C:
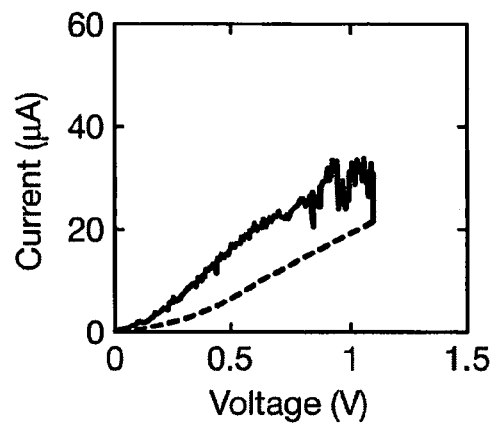
Figure 6D:
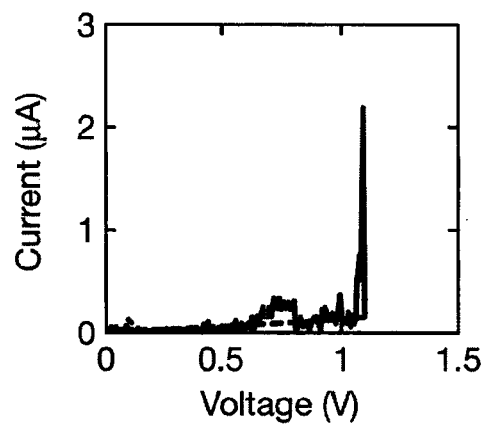
Figure 9:
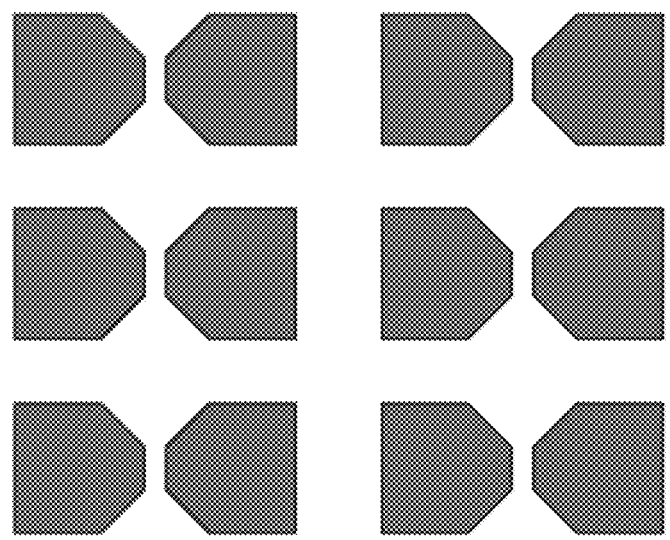

FIG. 9 shows a nano-gap array with a number of notched ribbons of graphene (such as the one shown in FIG. 4) arranged in an array.

DETAILED DESCRIPTION OF THE INVENTION

Example 1

Preparation of Device Containing Notched Ribbons of Graphene

Graphene devices were fabricated using a passive-first active-last process flow, where the graphene is transferred onto a pre-patterned silicon chip as illustrated in FIGS. 1(a-d). Such a passive-first active-last fabrication process enables integration of graphene into conventional silicon logic circuits.

Figure 1A:
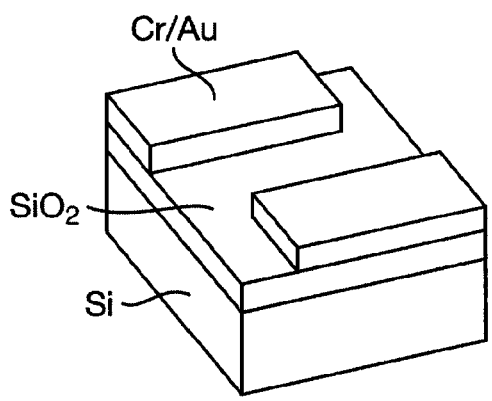
FIG. 1:(a)-(d) show schematics for the process flow of device fabrication according to the invention.
FIG. 1(e) shows a scanning electron micrograph of a single layer graphene (SLG) notched ribbon between two Cr/Au contacts produced according to the invention.
FIG. 1(f) shows current-voltage (I-V) traces recorded during the feedback-controlled electroburning step.
Figure 1B:
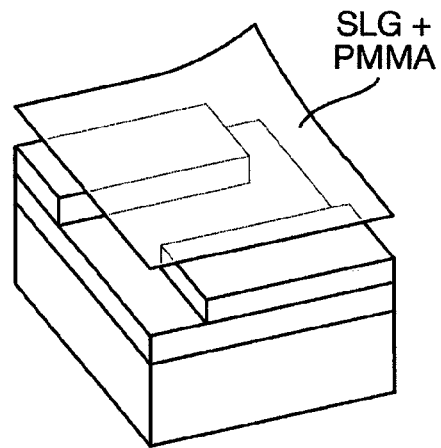
Figure 1C:
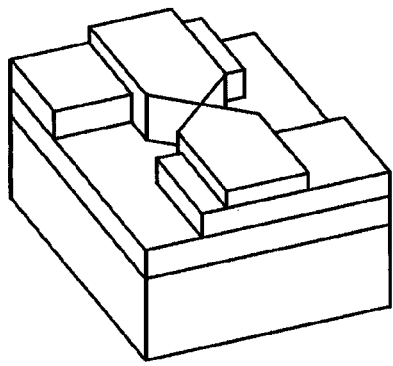
Figure 1D:
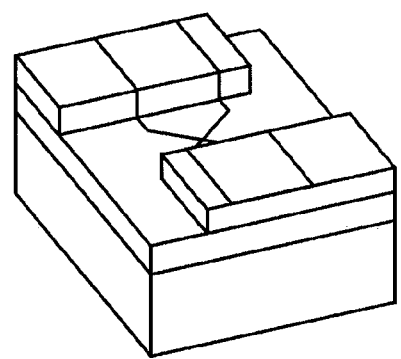
Figure 1E:
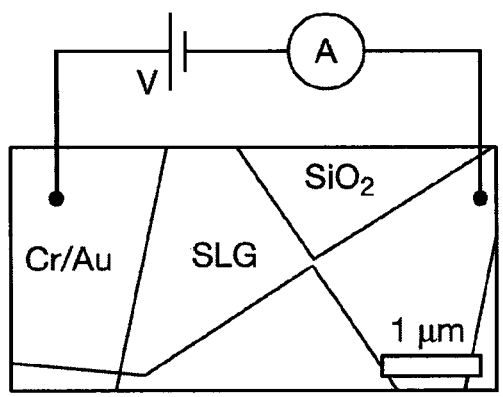

Single layer graphene (SLG) was prepared using a 1:4 $CH_4$:Ar gas mixture at atmospheric pressure on liquid copper in a CVD furnace at 1090° C. to form a SLG/copper stack. This method can produce large area single layer graphene. PMMA (poly methyl methacrylate) was spun across the SLG/copper stack before etching the copper away with a 0.1M solution of ammonium persulfate to produce a PMMA/SLG stack. The PMMA/graphene stack was rinsed in deionised water before being transferred onto a pre-patterned 1×1 $cm^2$ Si/$SiO_2$ chip (FIG. 1(a-b)). Each chip contained 540 pairs of Cr/Au electrodes that were patterned using electron beam lithography and metal evaporation. After the SLG was transferred onto the metal electrodes, it was patterned into notched ribbons by exposing a negative resist using electron beam lithography followed by oxygen plasma etching (FIG. 1(c-d)). The devices were then annealed at 350° C. for 1 hour in an Ar atmosphere to remove residual resist. FIG. 1(e) shows a scanning electron micrograph of a resulting SLG notched ribbon between two Cr/Au electrodes.

Example 2

Electroburning of Notched Graphene Ribbon to Form Nano-Gap

Feedback-controlled electroburning was performed on the devices fabricated in Example 1 in air at room temperature using an automated probe-station. The electroburning process comprised application of a voltage (V) across the devices which was ramped up at a rate of 0.75 V/s, while the current (I) was recorded with a 200 µs sampling rate. When the feedback condition (which was set at a drop Δ/set of the current within the past 15 mV) was met, the voltage was ramped down to zero at a rate of 225 V/s. After each voltage ramp the resistance of the SLG device was measured and the process was repeated until the low-bias resistance exceeded $R_{set}$ (e.g. 500 MΩ, which is 50 times higher than the resistance of one open transport channel). To prevent the SLG device from electroburning too abruptly at the initial voltage ramps, the feedback condition was adjusted for each voltage ramp depending on the threshold voltage Vth at which the previous current drop occurred. The feedback conditions used were $\Delta I_{set}$=6, 9, 12 and 15 µA for Vth≥1.6, 1.3 and 1.0 V respectively.

Figure 1F:
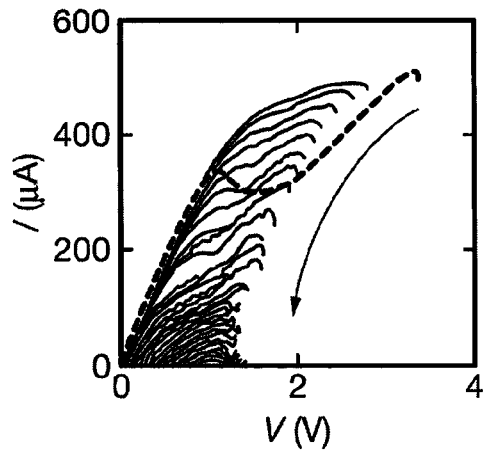

A typical evolution of the current-voltage (I-V) traces from Example 2 is shown in FIG. 1(f). The first voltage ramp (grey trace in FIG. 1(f)) shows a distinct region of negative differential conductance (NDC). Regions of NDC or 'kinks' in the I-V characteristics of single layer graphene devices are a characteristic feature of bipolar transport in single layer graphene. Typically, graphene on $SiO_2$ is p-doped, with holes being the majority carriers throughout the entire channel. When the source-drain voltage V is increased, the current starts to saturate as the electrochemical potential at the drain end of the channel moves towards the Dirac point. At a particular voltage V'kink', the electrochemical potential at the drain end corresponds to the Dirac point resulting in a pinch-off at the drain contact. By increasing V beyond V'kink' the pinch-off is moved through the channel until the entire channel switches to electron carriers and the current will increase again. The value for V'kink' is dependent on the relative position of the Fermi level from the Dirac point for the graphene electrodes, and is therefore dependent on the doping level. The observed a shift of V'kink' towards lower source-drain voltages with each electroburning voltage ramp event may be attributed to the removal of residual resist from current annealing. The removal of residual resist shifts the Fermi level closer towards the Dirac point which corresponds to the shift of V'kink' towards lower voltages. This increase in conductance has previously been observed in electroburning of few-layer graphene flakes and is attributed to the removal of residual resist by Joule heating of the graphene. From the AFM image of the device in FIG. 3, it can be observed that close to the notched region, the graphene is much cleaner compared to regions further away. This is an indication of residual resist removal from current annealing during the electroburning process.

Example 3

Characterisation of Nano-Gaps Via I-V Curves

Figure 2:
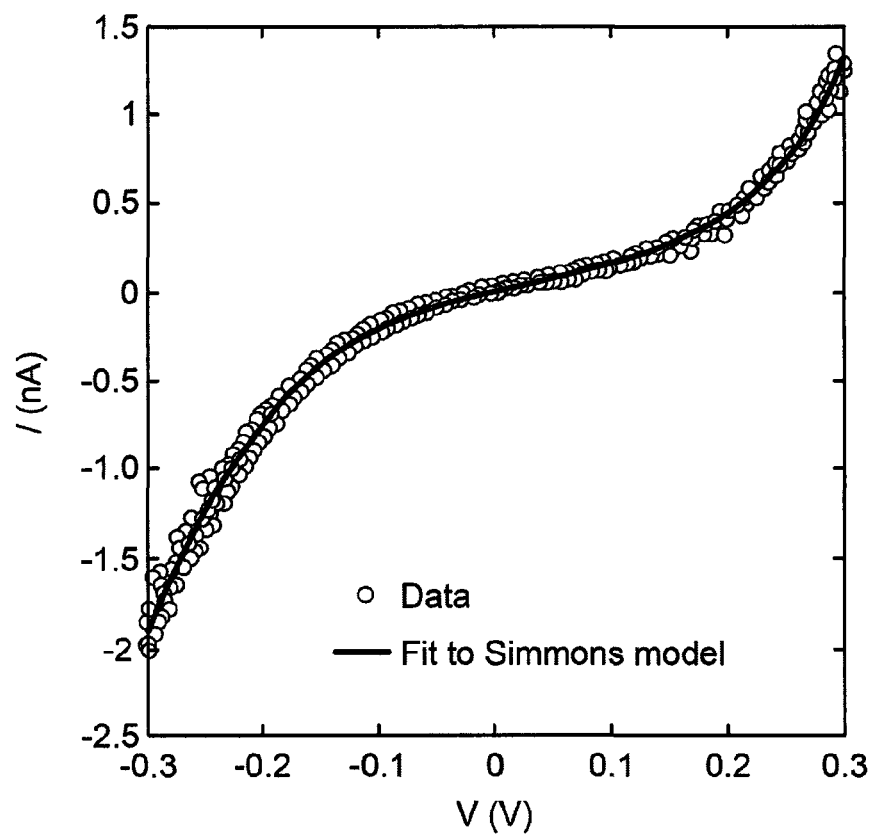
FIG. 2: Typical I-V trace of a SLG nano-gap. The I-V trace was fitted to the Simmons model for tunnelling through a trapezoidal barrier with the fitting parameters: barrier height $\varphi=0.26$ eV; barrier width (gap-size) d=1.50±0.03 nm; and barrier asymmetry $\alpha=-0.89\pm0.05$. A fit to the Simmons model of 328 devices yields an average gap-size of 0.5-2.5 for 96.5%.

The geometry of the nano-gaps formed in Example 2 was characterized by measuring the current-voltage curves using the same set-up used for the feedback controlled electroburning in Example 2. FIG. 2 shows a typical I-V trace of a SLG nano-gap after completion of the electroburning process, i.e. after the low-bias resistance becomes larger than Rset. The non-Ohmic I-V traces measured after the electroburning process are characteristic of transport through a single tunnel junction. The size of the tunnel-barrier can be estimated by fitting the I-V traces to the Simmons model using the barrier height, width and asymmetry as fitting parameters. The controllability and reproducibility of the nano-gap fabrication process were investigated by fitting 328 devices to the Simmons model. The average gap-size of 156 devices that underwent the electroburning process with a stop condition $R_{crit}$=300 MΩ was d=1.45±0.58 nm. For the 172 devices that were processed with a stop condition $R_{crit}$=500 MΩ, the gap-size was d=1.38±0.46 nm. 96.5% of 328 devices fitted return a gap-size within the range of 0.5-2.5 nm, which make these graphene nano-gaps appealing for contacting single molecules in molecular devices. The average fitted barrier heights was 0.24±0.10 eV. These compare with barrier heights observed in electroburned few-layer graphene nano-gaps and in electromigrated metal electrodes.

Table 1 gives an overview of the success rate of the electroburning process for a total number of 1079 devices on 5 chips. Three ways in which the electroburning process can fail have been identified: i) the current required to start the electroburning process is larger than the maximum current supplied by the voltage source used; ii) the feedback-control did not ramp the voltage back to zero fast enough, resulting in a nano-gap with an infinite resistance (>100 GΩ); iii) the feedback-control is too sensitive and ramps the voltage before electroburning occurs. Whereas the second and third failures are intrinsic to the feedback-controlled electroburning process, the first failure occurs if the lithographically defined notch is too wide. Because the first failure is not intrinsic to the electroburning process and could be overcome by using a different voltage source, the yield of the electroburning process has been defined by only considering those devices where the threshold current is within the range of our set-up. Using this definition, the yield of the electroburning process is 85%.

TABLE 1

Fabrication yield of the feedback-controlled electroburning process:

|  | Number of devices |
|---|---|
| Devices before electroburning | 1079 |
| Threshold current too high | 167 |
| Feedback not fast enough | 67 |
| Feedback too sensitive | 69 |
| Nano-gaps after electroburning | 776 |

Example 4

Further Characterisation of Nano-gaps Using Atomic Force Microscopy (AFM)

To further investigate the formation of the nano-gaps, AFM was perform ed on several devices prepared according to Examples 1 and 2 after the electroburning process. FIG. 3(a,b) shows an AFM image of an electroburned nano-gap. The AFM images show that the nano-g a p forms at the narrowest part of the notch. Without wishing to be bound by theory, this is thought to be due to the fact that the current density, and therefore the Joule heating, will be largest at this point. The breakdown current was determined as the current at which the feedback condition is met for the first voltage ramp. The breakdown current for the device shown in FIG. 3(a,b) is 310 μA, which corresponds to a current density $j=4.7\times10^8$ A/cm$^2$ (assuming a van der Waals thickness of 0.355 nm as sheet thickness). Breakdown current densities of $j=5\times10^8$ A/cm$^2$ have been reported for mechanically exfoliated SLG. For 1079 devices, an average breakdown current of 324±163 pA was found.

The formation of the nano-gaps is expected to be mediated by the breaking of carbon bonds at the graphene edges because of the higher reactivity of the edge-carbon atoms due to incomplete sp$^2$-hybridization. Thus, a gradual narrowing of the entire notch region could be expected. Surprisingly, the nano-gap formation process of the present invention proceeds via a crack developing across the narrowest region of the notch (see FIG. 3(d)).

Figure 3A:
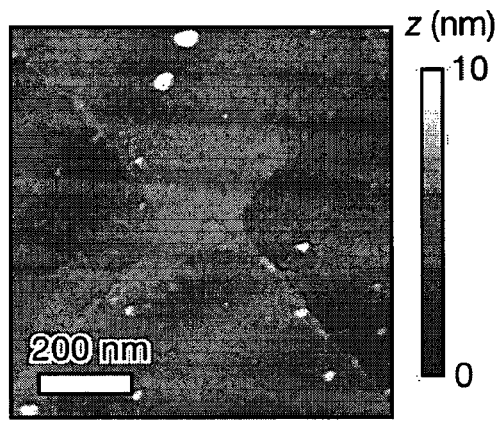
FIG. 3:(a,b) shows AFM images of a typical graphene nano-gap after the electroburning process. Light areas are graphene and dark areas are the $SiO_2$ substrate. A gap can be clearly discerned in the narrowest part of the notch. Close to the notch, the graphene flake is free of residual resist due to current annealing. 3(c) shows calculated current density profile for a pristine device. The thick solid lines indicate the edges of the device, the narrow stream lines illustrate the current flow. 3(d) shows calculated current density profile in the case of a partially formed nano-gap. The current flows around the cracks extending inwards from the notch apex resulting in a 'hotspot' at the crack-tip.
Figure 3B:
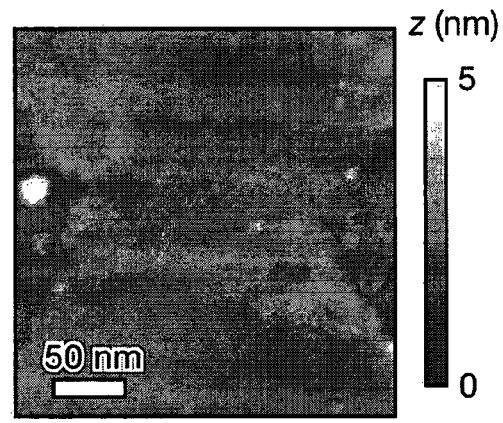
Figure 3C:
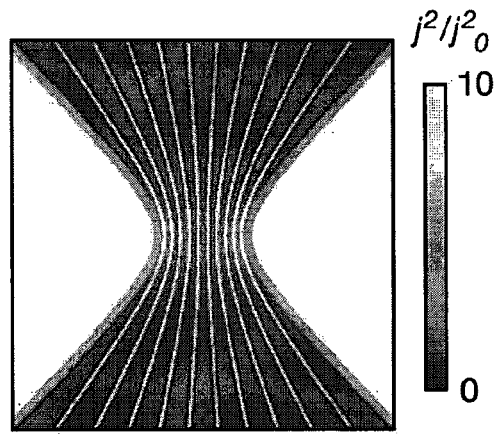
Figure 3D:
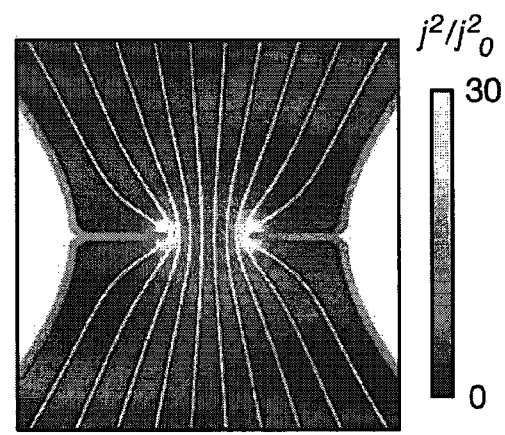

Nano-gap formation was further investigated by calculating the current density profile in the graphene notch. To calculate the current density (j(r)=∇ρ(r), where ρ(r) is the charge density) as function of position r, the Laplace equation $\nabla^2\rho(r)=0$ was solved using conformal mapping. The current density was highest at the apex of the notch (see FIG. 3(c)), which is where the formation of the nano-gap was observed experimentally. FIG. 3(d) shows the current flow around a crack extending from the apex of each notch, which was calculated using a Schwarz transformation. Since the current is forced to flow around the cracks, the current density is highest at the crack-tip. This may explain why, once a crack forms at the apex of the notch, it propagates through the material in accordance with our observations, rather than becoming wider. It also explains why the asymmetrical notch geometries in FIG. 5 can be used to grow a crack from a notch towards the other edge of the graphene ribbon. The calculations and experimental findings therefore demonstrate the ability to lithographically control the position of the nano-gaps, which allows for the precise alignment of the nano-gaps with other lithographically defined structures.

Example 5

Figure 7A:
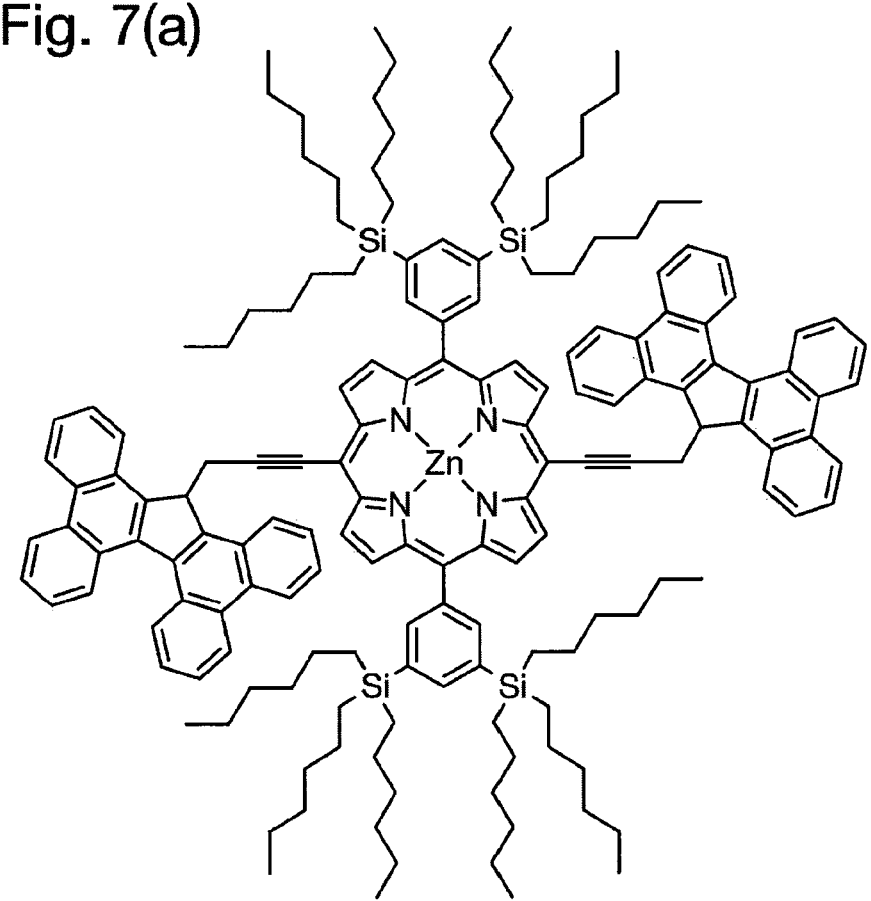
FIG. 7: Single-molecule transistor based on self-alignment of a zinc-porphyrin molecule with graphene nano-electrodes.
Figure 7B:
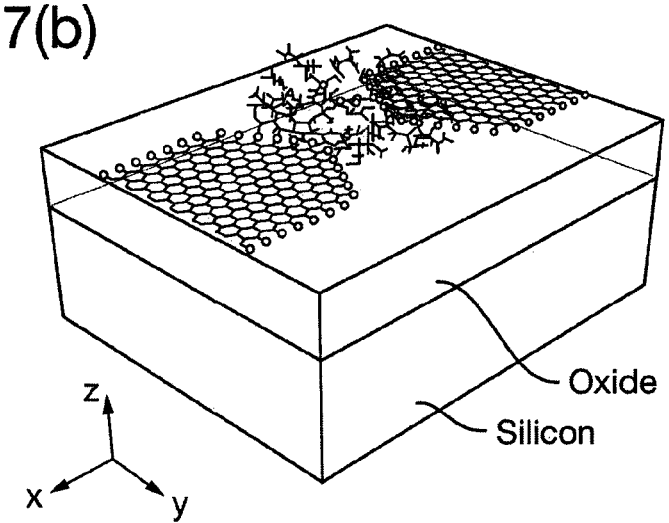
Figure 7C:
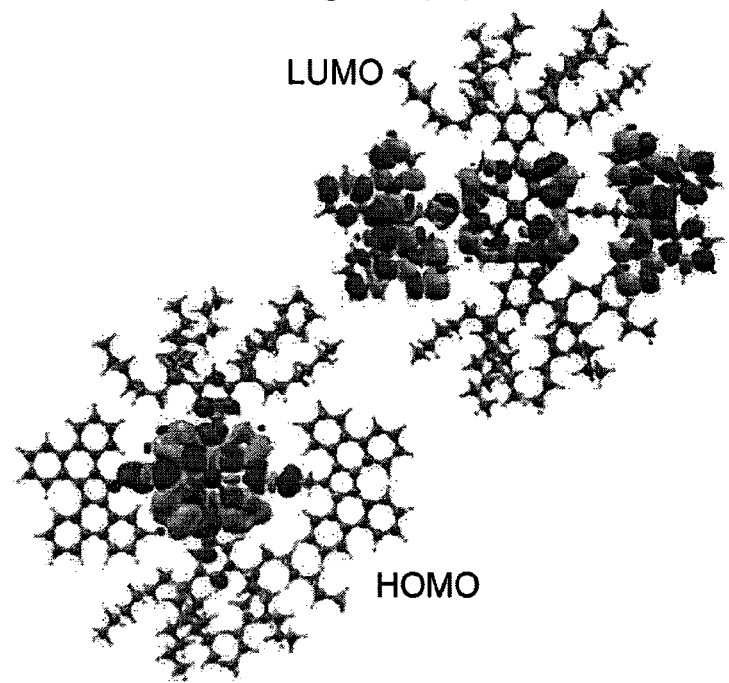
Figure 7D:
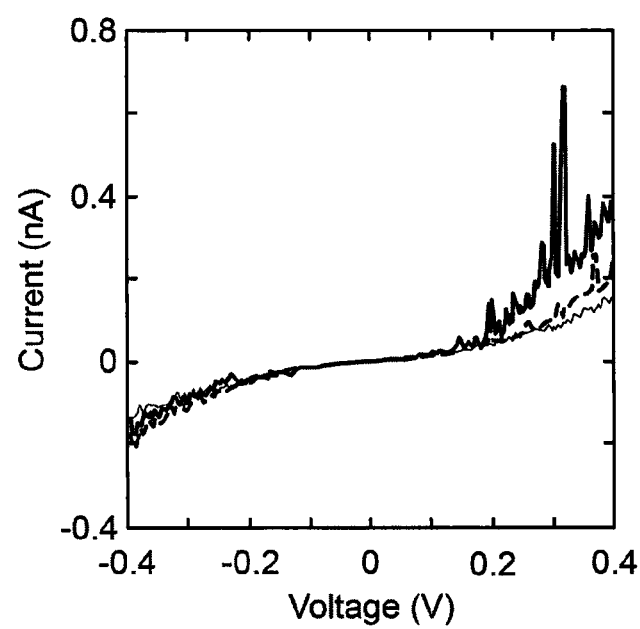

Single Molecule Transistor Based on Self-Alignment of a Zinc-Porphyrin Molecule with Graphene Nano-Electrodes Charge transport through individual molecules in a graphene-molecule-graphene junction, which works as a single-electron transistor (SET), was studied. A molecular wire, shown in FIG. 7a, consisting of a zinc-porphyrin back-bone (black in FIG. 7a) with tetrabenzofluorene anchors (green in FIG. 7a) was used. These "butterfly" limpet anchor groups have not previously been used in single-molecule devices. Density functional theory (DFT) calculations shown in FIG. 7b revealed that the molecular wires relaxes across the graphene nano-gap in a planar geometry. DFT calculations further indicate that the wave-functions of the highest occupied molecular orbital (HOMO) are delocalised over the porphyrin backbone and anchor groups, in contrast to the lowest unoccupied molecular orbital (LUMO) where they are only localised over the porphyrin backbone as shown in FIG. 7c. Overlap between the delocalised electron wave-functions of the fully conjugated zinc-porphyrin system with the butterfly anchors allows for electron transport through the wire. The molecular backbone is separated from the butterfly anchor groups by a —C≡C—CH$_2$— spacer (blue, -≡- in FIG. 7a), which allows the anchor groups to bind to the defect-free graphene rather than to the graphene edges. In addition to the butterfly limpets, the molecule has two hydrophobic side-groups (red, i.e. containing Si, in FIG. 7a). The side-groups make the molecular wire more soluble and prevent the central porphyrin from binding to the graphene electrodes. The graphene electrodes were fabricated using feedback-controlled electroburning as in Examples 1 and 2 and were typically separated by a 1-2 nm nano-gap. The chemical potential of the molecular wire was electrostatically tuned using the conducting silicon substrate as a back-gate (see FIG. 7b), which was separated from the molecule and graphene electrodes by a 300 nm thick silicon-oxide layer, resulting in a SET device geometry.

First, reproducible single-electron transport through individual molecules was demonstrated and that single electron charging is determined by the molecule rather than the microscopic details of the electrodes was shown. Reproducible SET behavior was measured at 20 mK in 10 out of 48 devices on which the molecular wire described above was deposited, as shown in FIG. 8. It was found that for all devices, $E_{add}$=0.37±0:05 eV for the Coulomb diamond closest to equilibrium (zero gate voltage). In a control experiment, the same molecular backbone without the butterfly anchor groups was deposited and the results suggested that the molecules best bridge the gap when the anchor groups are present. The result in the control experiment implies that the SET behaviour of the 10 devices initially tested was due to one or more molecular wires bridging the nano-gap. Moreover, the control experiment allowed the exclusion of carbon islands left over from an incomplete electroburning process as a possible source of the observed SET behaviour. Due to the stochastic nature of the electroburning process, island sizes are expected to differ for each device, which would result in varying addition energies for all devices. Similarly, clusters of two or more molecules would result in variations of the addition energy. Based on the device statistics it was concluded that the measured SET behaviour of the devices shown in FIG. 7 was the result of charge transport through nominally identical single-molecule transistors. The experiment therefore shows the reproducibility of the nano-gap formation.

The horizontal axes in FIG. 8 are scaled by an effective lever arm a for comparison. This lever arm is a measure of the capacitive coupling between the gate and the molecule and differs from device to device. It was determined that α=0.006–0.04 from the slopes of the Coulomb diamonds for each single molecule transistor presented in FIG. 8.

The small values of a indicate that the total capacitance is dominated by the source and drain electrodes, and is consistent with electrostatic calculations. The variation in a can be attributed to differences in screening of the gate-field by the source and drain electrodes. The gate voltage to align the electrochemical potential of the electrodes within the Dirac point is greater than 40 V, thus giving an upper limit to the shift in the electrochemical potential of the electrodes as less than half the change in the potential of the molecule deduced from the slope of the Coulomb diamonds. Variations in the current through different devices may be attributed to differences in overlap between the anchor groups and the graphene electrodes.

It was shown that the molecules were well centered between the source and drain electrode, i.e. well-aligned in the nano-gap. The experiments demonstrate room-temperature charge- and energy-quantization in a reproducible graphene-molecule-graphene device geometry. The modular design of the molecular wire makes this approach applicable to a wide variety of molecular backbones. Specifically, the π-π anchoring of the molecule to the highly stable graphene nano-electrodes allows high-bias energy spectroscopy of the excited states and removes the need for statistical analysis of ensemble measurements. The findings offer a route to a vast number of quantum transport experiments that are well established for semiconductor quantum dots, but at an energy-scale larger than kT at room temperature.

It should be apparent that the foregoing relates only to the preferred embodiments of the present application and the resultant patent. Numerous changes and modification may be made herein by one of ordinary skill in the art without departing from the general spirit and scope of the invention as defined by the following claims and the equivalents thereof.

We claim:

1. A method for preparing a nano-gap array on graphene, said method comprising:
    (i) depositing graphene onto a substrate;
    (ii) shaping the graphene such that it has a plurality of ribbons, each ribbon comprising a notch and an apex; and
    (iii) controlling the position of nano-gap formation in the graphene by feed-back-controlled electroburning which comprises applying a voltage across each apex, wherein a region across which the voltage is applied comprises a width which is the narrowest in that region, wherein the step of applying a voltage comprises:
        (a) increasing the voltage while recording the current or resistance;
        (b) decreasing the voltage when said current drops or said resistance increases; and
    repeating steps (a) and (b) until a nano-gap has formed;
    wherein the nano-gap forms via a crack developing across the graphene that extends from each apex of each notch thus forming an array of nano-gaps, each of which extends across the entire width of the graphene.

2. The method of claim 1, wherein said substrate is a silicon substrate which is patterned with electrical contacts.

3. The method of claim 1, wherein controlling the position of the nano-gap formation aligns a nano-gap with a lithographically defined structure.

4. The method of claim 1, wherein each notch comprises a V-shaped notch.

5. The method as claimed in claim 1 wherein the ribbon comprises an asymmetrical ribbon.

6. The method as claimed in claim 5, wherein the asymmetrical ribbon comprises the notch on a first side.

7. The method as claimed in claim 1 wherein said graphene is single layer graphene (SLG).

8. The method as claimed in claim 1 wherein the width of the nano-gap is determined by analyzing an I-V measurement.

9. The method as claimed in claim 1 wherein changes in a conductance are used to determine the onset of gap formation.

10. The method as claimed in claim 1 wherein the width of the nano-gap is 0.1 to 5 nm.

11. The method as claimed in claim 1 wherein the graphene is CVD-grown graphene.

12. The method as claimed in claim 1 wherein, prior to application of the voltage, the graphene is shaped lithographically.

13. The method as claimed in claim 1 wherein the width of the nano-gap is 0.5 to 2.5 nm.

14. The method as claimed in claim 1 wherein the width of the nano-gap is 1 to 2 nm.

* * * * *